United States Patent
Olson et al.

(10) Patent No.: US 11,116,503 B2
(45) Date of Patent: *Sep. 14, 2021

(54) CENTER CINCH AND RELEASE OF BUTTRESS MATERIAL

(71) Applicant: Covidien LP, Mansfield, MA (US)

(72) Inventors: Lee Ann Olson, Wallingford, CT (US); Ernest Aranyi, Easton, CT (US); Patrick D. Mozdzierz, Glastonbury, CT (US)

(73) Assignee: COVIDIEN LP, Mansfield, MA (US)

( * ) Notice: Subject to any disclaimer, the term of this patent is extended or adjusted under 35 U.S.C. 154(b) by 184 days.

This patent is subject to a terminal disclaimer.

(21) Appl. No.: 16/420,219

(22) Filed: May 23, 2019

(65) Prior Publication Data

US 2019/0274685 A1   Sep. 12, 2019

Related U.S. Application Data

(63) Continuation of application No. 15/251,773, filed on Aug. 30, 2016, now Pat. No. 10,327,772, which is a
(Continued)

(51) Int. Cl.
*A61B 17/072* (2006.01)
*A61B 17/068* (2006.01)
*A61B 17/04* (2006.01)

(52) U.S. Cl.
CPC .... *A61B 17/07207* (2013.01); *A61B 17/0469* (2013.01); *A61B 17/0682* (2013.01);
(Continued)

(58) Field of Classification Search
CPC .......... A61B 17/07207; A61B 17/0469; A61B 17/0682; A61B 17/07292
(Continued)

(56) References Cited

U.S. PATENT DOCUMENTS 3,054,406 A   9/1962   Usher
3,079,606 A   3/1963   Bobrov et al.
(Continued)

FOREIGN PATENT DOCUMENTS

CA   2282761 A1   9/1998
CA   2 667 434 A1   5/2008
(Continued)

OTHER PUBLICATIONS

Chinese First Office Action corresponding to Patent Application CN 201410588811.8 dated Dec. 5, 2017.
(Continued)

*Primary Examiner* — Nathaniel C Chukwurah
(74) *Attorney, Agent, or Firm* — Carter, DeLuca & Farrell LLP (57) ABSTRACT

A buttressed anvil assembly is provided for use with a surgical stapling instrument. The buttressed anvil assembly generally includes an anvil member having a strip of buttress material attached thereto by a pair of sutures. A tensioning mechanism is provided to secure or tension the buttress material to the anvil member prior to use and allow for release of the buttress material after stapling of tissue. The tensioning mechanism includes a cinch track engageable with one of the pair of sutures.

20 Claims, 5 Drawing Sheets

Related U.S. Application Data continuation of application No. 13/904,652, filed on May 29, 2013, now Pat. No. 9,445,812, which is a continuation of application No. 13/545,031, filed on Jul. 10, 2012, now Pat. No. 8,453,909, which is a continuation of application No. 13/111,050, filed on May 19, 2011, now Pat. No. 8,235,273, which is a continuation of application No. 12/414,961, filed on Mar. 31, 2009, now Pat. No. 7,967,179.

(52) U.S. Cl.
CPC .............. *A61B 17/07292* (2013.01); *A61B 2017/07214* (2013.01); *A61B 2017/07257* (2013.01); *A61B 2017/07271* (2013.01); *A61B 2017/07285* (2013.01)

(58) Field of Classification Search
USPC ...................................................... 227/180.1
See application file for complete search history.

(56) References Cited

U.S. PATENT DOCUMENTS

| | | |
|---|---|---|
| 3,124,136 A | 3/1964 | Usher |
| 3,490,675 A | 1/1970 | Green et al. |
| 3,499,591 A | 3/1970 | Green |
| 3,797,494 A | 3/1974 | Zaffaroni |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,476,206 A | 12/1995 | Green et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,142,933 A | 11/2000 | Longo et al. |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,610,006 B1 | 8/2003 | Amid et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 * | 12/2006 | Shelton, IV ...... A61B 17/07207 227/176.1 |
| 7,160,299 B2 | 1/2007 | Baily |
| 7,179,268 B2 | 2/2007 | Roy et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |

(56) References Cited

U.S. PATENT DOCUMENTS

| | | | |
|---|---|---|---|
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,967,179 B2 * | 6/2011 | Olson | A61B 17/0682 227/175.1 |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,983 B2 | 10/2011 | Chu et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 * | 8/2012 | Olson | A61B 17/07292 227/175.1 |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 * | 6/2013 | Olson | A61B 17/0469 227/176.1 |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,328,111 B2 | 5/2016 | Zhou et al. |
| 9,351,729 B2 | 5/2016 | Orban, III et al. |
| 9,358,005 B2 | 6/2016 | Shelton, IV et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 * | 9/2016 | Olson | A61B 17/0682 |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |

(56) References Cited

U.S. PATENT DOCUMENTS

| | | |
|---|---|---|
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,327,772 B2 | 6/2019 | Olson et al. |
| 2002/0028243 A1 | 3/2002 | Masters |
| 2002/0091397 A1 | 7/2002 | Chen |
| 2002/0165559 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0283256 A1 | 12/2005 | Sommerich et al. |
| 2006/0004407 A1 | 1/2006 | Hiles et al. |
| 2006/0025816 A1 | 2/2006 | Shelton |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241499 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |

(56) References Cited

U.S. PATENT DOCUMENTS

| | | |
|---|---|---|
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2016/0045200 A1 | 2/2016 | Milliman |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |

FOREIGN PATENT DOCUMENTS

| | | |
|---|---|---|
| CN | 101310680 A | 11/2008 |
| CN | 101332110 A | 12/2008 |
| DE | 1602563 U | 3/1950 |
| DE | 19924311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2008595 A2 | 12/2008 |
| EP | 2039308 A2 | 3/2009 |
| EP | 2090231 A1 | 8/2009 |
| EP | 2090244 A2 | 8/2009 |
| EP | 2090252 A2 | 8/2009 |
| EP | 2163211 A2 | 3/2010 |
| EP | 2189121 A1 | 5/2010 |
| EP | 2198787 A1 | 6/2010 |
| EP | 2236098 A2 | 10/2010 |
| EP | 2236099 A1 | 10/2010 |
| EP | 2258282 A2 | 12/2010 |
| EP | 2292276 A2 | 3/2011 |
| EP | 2311386 A2 | 4/2011 |
| EP | 2436348 A1 | 4/2012 |
| EP | 2462880 A2 | 6/2012 |
| EP | 2491867 A1 | 8/2012 |
| EP | 2497431 A1 | 9/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |
| EP | 2644125 A2 | 10/2013 |
| EP | 2762091 A2 | 8/2014 |
| JP | 2000166933 A | 6/2000 |
| JP | 2002202213 A | 7/2002 |
| JP | 2007124166 A | 5/2007 |
| WO | 9005489 A1 | 5/1990 |
| WO | 95/16221 A1 | 6/1995 |
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |

(56) References Cited

FOREIGN PATENT DOCUMENTS

| WO | 2010075298 A2 | 7/2010 |
|---|---|---|
| WO | 2011143183 A2 | 11/2011 |
| WO | 2012044848 A1 | 4/2012 |

OTHER PUBLICATIONS

European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
European Search Report corresponding to EP 10 25 0715.9, completed Jun. 30, 2010 and dated Jul. 20, 2010; 3 pages.
European Search Report corresponding to EP 05 80 4382.9, completed Oct. 5, 2010 and dated Oct. 12, 2010; 3 pages.
European Search Report corresponding to EP 10 25 1437.9, completed Nov. 22, 2010 and dated Dec. 16, 2010; 3 pages.
European Search Report corresponding to EP 09 25 2897.5, completed Feb. 7, 2011 and dated Feb. 15, 2011; 3 pages.
European Search Report corresponding to EP 10 25 0642.5, completed Mar. 25, 2011 and dated Apr. 4, 2011; 4 pages.
European Search Report corresponding to EP 11 18 8309.6, completed Dec. 15, 2011 and dated Jan. 12, 2012; 3 pages.
European Search Report corresponding to EP 12 15 2229.6, completed Feb. 23, 2012 and dated Mar. 1, 2012; 4 pages.
European Search Report corresponding to EP 12 15 0511.9, completed Apr. 16, 2012 and dated Apr. 24, 2012; 7 pages.
European Search Report corresponding to EP 12 15 2541.4, completed Apr. 23, 2012 and dated May 3, 2012; 10 pages.
European Search Report corresponding to EP 12 16 5609.4, completed Jul. 5, 2012 and dated Jul. 13, 2012; 8 pages.
European Search Report corresponding to EP 12 15 8861.0, completed Jul. 17, 2012 and dated Jul. 24, 2012; 9 pages.
European Search Report corresponding to EP 12 16 5878.5, completed Jul. 24, 2012 and dated Aug. 6, 2012; 8 pages.
Extended European Search Report corresponding to EP 12 19 1035.0, completed Jan. 11, 2013 and dated Jan. 18, 2013; 7 pages.
Extended European Search Report corresponding to EP 12 18 6175.1, completed Jan. 15, 2013 and dated Jan. 23, 2013; 7 pages.
Extended European Search Report corresponding to EP 12 19 1114.3, completed Jan. 23, 2013 and dated Jan. 31, 2013; 10 pages.
Extended European Search Report corresponding to EP 12 19 2224.9, completed Mar. 14, 2013 and dated Mar. 26, 2013; 8 pages.
Extended European Search Report corresponding to EP 12 19 6911.7, completed Apr. 18, 2013 and dated Apr. 24, 2013; 8 pages.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
Chinese Office Action issued in Chinese Application No. 201410449019.4 dated Mar. 30, 2016.
Chinese First Office Action corresponding to counterpart Int'l Appln. No. CN 201310706871.0 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 201310303690.3 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Extended European Search Report corresponding to EP 08 72 6500.5, completed Feb. 20, 2014 and dated Mar. 3, 2014;(7 pp).
Extended European Search Report corresponding to EP 13 19 5919.9, completed Feb. 10, 2014 and dated Mar. 3, 2014; (7 pp).
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.

(56) References Cited

OTHER PUBLICATIONS

Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 79585 dated Dec. 11, 2017.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 4995.0, completed Jun. 5, 2014 and dated Jun. 16, 2014; (5 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014; (8 pp).
Extended European Search Report corresponding to EP 14 15 7195.0, completed Jun. 5, 2014 and dated Jun. 18, 2014; (9 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 48145 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report correspponding to EP 12 19 1035.0, completed Jan. 11, 2013 and dated Jan. 18, 2013; 7 pages.
Extended European Search Report correspponding to EP 12 19 6904.2, completed Mar. 28, 2013 and dated Jul. 26, 2013; 8 pages.
Extended European Search Report correspponding to EP 12 19 8749.9, completed May 21, 2013 and dated May 31, 2013; 8 pages.
Extended European Search Report correspponding to EP 07 00 5842.5, completed May 13, 2013 and dated May 29, 2013; 7 pages.
Extended European Search Report correspponding to EP 12 19 8776.2, completed May 16, 2013 and dated May 27, 2013; 8 pages.
Extended European Search Report correspponding to EP 13 15 6297.7, completed Jun. 4, 2013 and dated Jun. 13, 2013; 7 pages.
Extended European Search Report correspponding to EP 13 17 3985.6, completed Aug. 19, 2013 and dated Aug. 28, 2013; 6 pages.
Extended European Search Report correspponding to EP 13 17 3986.4, completed Aug. 20, 2013 and dated Aug. 29, 2013; 7 pages.
European Search Report corresponding to EP 05 02 2585.3, completed Jan. 25, 2006 and dated Feb. 3, 2006; 4 pages.
European Search Report corresponding to EP 06 00 4598, dated Jun. 22, 2006; 2 pages.
European Search Report corresponding to EP 06 01 6962.0, completed Jan. 3, 2007 and dated Jan. 11, 2007; 10 pages.
International Search Report corresponding to International Application No. PCT/US2005/036740, completed Feb. 20, 2007 and dated Mar. 23, 2007; 8 pages.
International Search Report corresponding to International Application No. PCT/US2007/022713, completed Apr. 21, 2008 and dated May 15, 2008; 1 page.

(56) References Cited

OTHER PUBLICATIONS

International Search Report corresponding to International Application No. PCT/US2008/002981, completed Jun. 9, 2008 and dated Jun. 26, 2008; 2 pages.
European Search Report corresponding to EP 08 25 1779, completed Jul. 14, 2008 and dated Jul. 23, 2008; 5 pages.
European Search Report corresponding to EP 08 25 1989.3, completed Mar. 11, 2010 and dated Mar. 24, 2010; 6 pages.
European Search Report corresponding to EP 10 25 0639.1, completed Jun. 17, 2010 and dated Jun. 28, 2010; 7 pages.
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.

\* cited by examiner

CENTER CINCH AND RELEASE OF BUTTRESS MATERIAL

CROSS REFERENCE TO RELATED APPLICATIONS

The present application is a Continuation Application of U.S. patent application Ser. No. 15/251,773, filed Aug. 30, 2016, now U.S. Pat. No. 10,327,772, which is a Continuation Application of U.S. patent application Ser. No. 13/904, 652, filed May 29, 2013, now U.S. Pat. No. 9,445,812, which is a Continuation Application of U.S. patent application Ser. No. 13/545,031, filed Jul. 10, 2012, now U.S. Pat. No. 8,453,909, which is a Continuation Application of U.S. patent application Ser. No. 13/111,050, filed May 19, 2011, now U.S. Pat. No. 8,235,273, which is a Continuation Patent Application which claims priority to, and the benefit of, U.S. patent application Ser. No. 12/414,961 filed on Mar. 31, 2009, now U.S. Pat. No. 7,967,179, the entire contents of each of which are incorporated herein by reference.

TECHNICAL FIELD

The present disclosure relates to an anvil assembly incorporating a strip of buttress material for use with a surgical stapling instrument. More particularly, the present disclosure relates to a buttress release mechanism for release of the buttress material from the surgical stapling instrument after stapling.

BACKGROUND

During various surgical procedures it is often necessary to join two sides of tissue. This is typically accomplished by approximating two edges of the tissues flush against one another and securing them by stapling, suturing, etc. In some instances, the staple or suture line connecting the tissues may tear or tend to pull through the tissues, particularly, where the tissues are diseased and relatively weak. Additionally, during healing, leakage may occur through the staple or suture lines.

In order to alleviate these problems, a strip of material, called "buttress material" is positioned against the tissues prior to stapling or suturing. The buttress material tends to reinforce the staple or suture line as well as tend to prevent leakage prior to healing.

The buttress material may be attached to the surgical instrument being used. For example, the buttress material is often pre-attached to a staple cartridge or anvil assembly of a surgical stapling instrument. The attachment of the buttress material needs be sufficiently secure to allow the surgical instrument to be inserted into the body of a patient as well as allowing the staple cartridge and anvil to be positioned about specific tissues to be stapled. Furthermore, after stapling of the tissues, the buttress material needs to be attached in a manner which allows easy separation of the buttress material from the associated staple cartridge and/or anvil.

Therefore, it is desirable to provide a cartridge or anvil assembly which is capable of easily releasing the buttress material after tissues have been stapled.

SUMMARY

There is disclosed a buttressed anvil assembly for use with a surgical stapling instrument. The buttressed anvil assembly generally includes an anvil having a strip of buttress material positioned adjacent a bottom side of the anvil. Distal and proximal sutures secure the buttress material to the anvil. A tensioning mechanism is provided at a distal end of the anvil assembly. The tensioning mechanism includes a cinch track engageable with the distal suture to hold a distal end of the strip of buttress material against the anvil. The cinch track is movable between a first vertical position tensioning the distal suture against the strip of buttress material to a second vertical position releasing tension on the distal suture to allow release of the strip of buttress material from the anvil.

A release member is provided in the anvil to move the cinch track between the first vertical position and the second vertical position. The release member includes a wedge engageable within a slot formed in the cinch track. A wedge is movable between a first horizontal position maintaining the cinch track in the first vertical position and a second horizontal position allowing the cinch track to move to the second vertical position. A proximal suture may also be provided to secure a proximal end of the strip of buttress material to a proximal end of the anvil.

Specifically, in a particular embodiment, the anvil assembly generally includes an anvil member having a first side and a second side and a length of suture material passing from the first side of the anvil member to the second side of the anvil member. A cinch track is movably mounted on the first side of the anvil member and is engageable with the length of suture. The cinch track is movable between a first vertical position tensioning the length of suture and a second vertical position releasing tension on the length of suture. A release member is movably mounted on the first side of the anvil member and is movable relative to the cinch track between a first horizontal position and a second horizontal position. The release member maintains the cinch track in the first vertical position when the release member is in the first horizontal position and allows the cinch track to move to the second vertical position when the release member is in the second horizontal position.

The anvil assembly additionally includes a strip of buttress material positioned adjacent the second side of the anvil member. The length of suture includes a backspan and first and second suture sides extending from the backspan. The backspan is engageable with the strip of buttress material to maintain the strip of buttress material adjacent the second side of the anvil member when the cinch track is in the first vertical position.

The anvil member includes first and second holes extending between the first and second sides of the anvil member. The first side of the length of suture material extends through the first hole and the second side of the suture material extends through the second hole. The cinch track includes a first track and the first suture side is secured in the first track. The cinch track also includes a second track and the second suture side is secured in the second track.

The release member includes a wedge and the cinch track includes a slot such that the cinch track is in the first vertical position when the wedge is positioned within the slot and is in the second vertical position when the wedge is out of the slot. The anvil member includes a longitudinally extending slot and the release member includes a guide rib movable within the longitudinally extending slot.

The strip of buttress material includes a perforation line adjacent a distal end of the buttress material to allow separation of the buttress material distally of the anvil slot. The strip of buttress material includes first and second cutouts to accommodate passage of the first and second sides of the length of suture material.

The anvil assembly additionally includes a proximal length of suture material for securing a proximal end of the strip of buttress material to the anvil member. The proximal length of suture material includes a backspan and first and second sides extending from the backspan. The backspan secures a proximal end of the strip of buttress material to the second side of the anvil member. The anvil member includes a pair of slots adjacent the proximal end of the anvil member. The pair of slots is dimensioned to frictionally secure the first and second sides of the proximal length of suture material. The strip of buttress material includes first and second cutouts formed adjacent the proximal end of the strip of buttress material for passage of the first and second sides of the proximal length of suture material.

The anvil assembly further includes a cover affixed to the anvil member. The cover including a distal window providing visualization of the cinch track and a pair of proximal windows providing visualization of the first and second sides of the proximal length of suture material secured within the first and second slots formed in the anvil member.

DESCRIPTION OF THE DRAWINGS

An embodiment of the presently disclosed buttressed anvil assembly is disclosed herein with reference to the drawings, wherein.

DETAILED DESCRIPTION

An embodiment of the presently disclosed buttressed anvil assembly will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
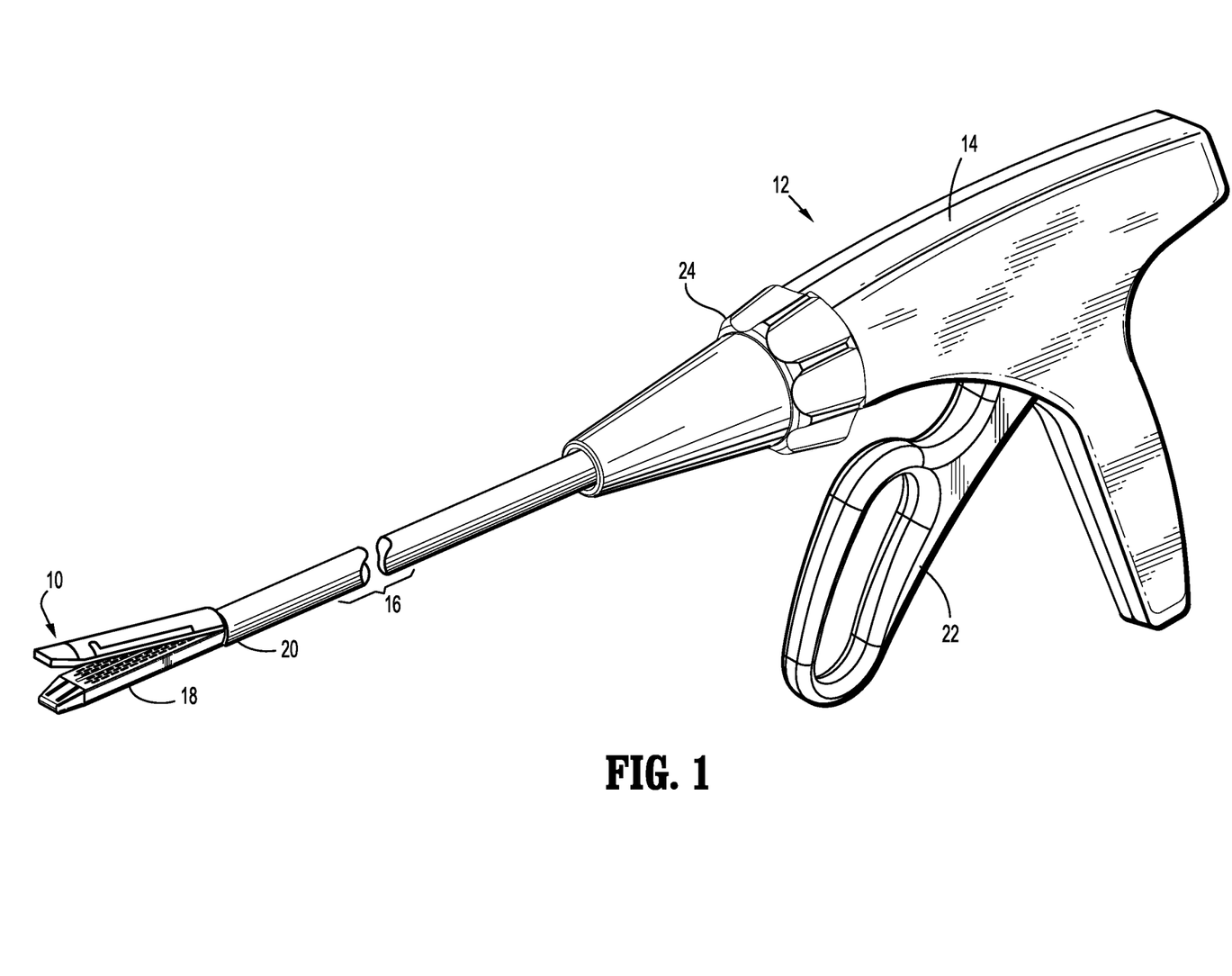
FIG. 1 is a perspective view of a surgical stapling instrument incorporating a buttressed anvil assembly.

Referring to FIG. 1, there is disclosed a buttressed anvil assembly or anvil assembly 10 for use with a surgical stapling instrument 12. As used herein, "buttress" includes pledgets, staple line reinforcement material, gaskets, and other materials used in conjunction with surgical instruments for joining tissue. Surgical stapling instrument 12 is a type well known in the art and is embodied in U.S. Pat. Nos. 5,762,256; 5,782,396; and 6,032,849, the contents of which are expressly incorporated herein by reference.

Surgical stapling instrument 12 generally includes a pistol grip body portion 14 having an elongate tubular member 16 extending distally from body portion 14. A staple cartridge 18 is mounted on a distal end 20 of elongate tubular member 16. Anvil assembly 10 is movably mounted on a distal end 20 of elongate tubular member 16 and is movable between an open position spaced apart from staple cartridge 18 to a closed position wherein anvil assembly 10 is in close cooperative alignment with staple cartridge 18.

In order to move anvil assembly 10 between the open and closed positions, surgical stapling instrument 12 includes a trigger 22 pivotally mounted to body portion 14. Trigger 22 controls the linear movement of an actuation shaft (not shown) which is mounted within the elongated tubular member 16. The actuation shaft operates to move a drive beam (not shown) distally to initially move the anvil assembly 10 between the open and closed positions. The drive beam also acts to move an actuation sled (not shown) distally through the staple cartridge 18 to eject staples. The drive beam includes a knife blade to cut tissue as the drive beam translates through the staple cartridge 18. A rotation knob 24 is provided to orient anvil assembly 10 and staple cartridge 18 relative to the tissue being stapled.

Although surgical stapling instrument 12 is shown with a single trigger 22 which accomplishes both jaw closure and firing of staples, it is further contemplated that the present buttress release mechanism can also be used with surgical stapling instruments of the type which utilize a clamping mechanism to close the jaws which is separate from the firing mechanism. See, for example, U.S. Pat. No. 5,476,206, the contents of which are expressly incorporated herein by reference.

Figure 2:
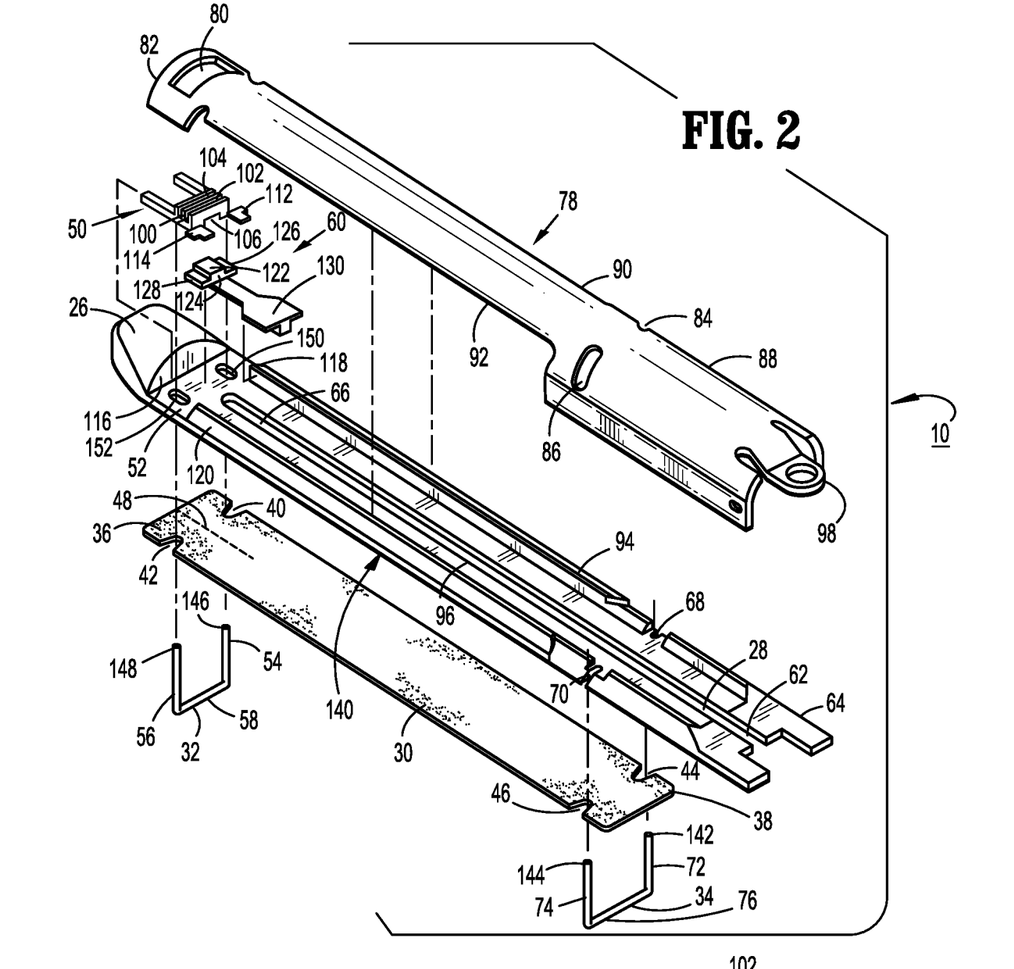
FIG. 2 is a perspective view, with parts separated, of the buttressed anvil assembly incorporating a strip of buttress material.

Referring now to FIG. 2, anvil assembly 10 generally includes an anvil member 26, having a knife slot 28 extending longitudinally partially through anvil member 26, and a length or strip of buttress material 30. Strip of buttress material 30 is secured to anvil member 26 by a first or distal suture 32 and a second or proximal suture 34. Distal and proximal sutures 32 and 34 secure respective distal and proximal ends 36 and 38 of buttress material 30 to anvil member 26 in a manner described in more detail hereinbelow.

Buttress material 30 further includes a pair of distal cutouts 40 and 42 formed adjacent distal end 36 of buttress material 30. Distal cutouts 40 and 42 are provided to accommodate passage of distal suture 32 to secure buttress material 30 to anvil member 26 and prevent any distal movement of buttress material 30 relative to anvil member 26. Similarly, a pair of proximal cutouts 44 and 46 is formed adjacent proximal end 38 of buttress material 30. Proximal cutouts 44 and 46 are provided to receive proximal suture 34 to secure proximal end 38 of buttress material 30 to anvil member 26 and prevent any longitudinal motion of buttress material 30. It should be noted that, during stapling and cutting of tissue, distal end 36 of buttress material 30 is distal of knife slot 28 and thus is not cut. A perforation line 48 may be formed in distal end 36 to facilitate separation of buttress material 30 into two halves after tissue has been stapled and cut.

In order to maintain tension of distal suture 32 against buttress material 30 prior to the cutting of tissue and to allow for the release of tension of distal suture 32 against buttress material 30, anvil assembly 10 further includes a cinch track 50 which is positioned within a distal end 52 of anvil member 26. Cinch track 50 is movable between a first vertical position tensioning distal suture 32 against buttress material 30 and a second vertical position releasing tension of distal suture 32 against buttress material 30. Cinch track 50 is provided to securely engage first and second sides 54 and 56 of first suture 32. The suture can be preformed in a shape defining the first side 54, second side 56, and backspan 58, or can comprise an ordinary suture that is wrapped around the anvil so as to defining the first side 54, second side 56, and backspan 58. The backspan 58 of first suture 32 lies against the distal end 36 of buttress material 30 against anvil member 26.

In order to move cinch track 50 between the first and second vertical positions, a release member 60 is provided and is longitudinally or horizontally movable within anvil member 26 in a manner described in more detail hereinbelow. The release member 60 may be formed as a bar, rod, cable or other member.

As shown, knife slot 28 has a proximal end 62 which is open at proximal end 64 of anvil member 26. A distal end 66 of knife slot 28 terminates proximally of distal end 52 of anvil member 26. As noted herein above, buttress material 30 includes a perforation line 48 to facilitate separation of distal end 36 of buttress material 30 as it is located distally of distal end 66 of knife slot 28.

In order to secure a proximal end 38 of buttress material 30 against anvil member 26, anvil member 26 is provided with a pair of slots 68 and 70 which are configured to securely receive first and second sides 72 and 74 of proximal suture 34. The proximal suture can be preformed in a shape or comprise an ordinary suture wrapped around the anvil member so as to define first side 72, second side 74 and backspan 76. The backspan 76 of proximal suture 34 engages proximal end 38 of buttress material 30 to secure proximal end 38 against anvil member 26.

Anvil assembly 10 additionally includes an anvil cover 78 having a distal cinch window 80 formed in a distal end 82 of anvil cover 78. Distal cinch window 80 is provided to allow the surgeon to visually confirm the engagement of distal suture 32 with cinch track 50. A pair of proximal cinch windows 84 and 86 are provided adjacent proximal end 88 of anvil cover 78 and serve to allow the surgeon to visually confirm the engagement of proximal suture 34, specifically the engagement of first and second sides 72 and 74, with slots 68 and 70 formed in proximal end 64 of anvil member 26.

Anvil cover 78 includes longitudinally extending side cuts 90 and 92 which are configured to engage side walls 94 and 96, formed in anvil member 26, in friction fit fashion to secure anvil cover 78 to anvil member 26. Alternatively, the anvil cover may be attached using welding, adhesives or other means. Mounting structure 98 is provided on proximal end 88 to facilitate attachment of anvil assembly 10 to distal end 20 of elongate tubular member 16 (FIG. 1).

Figure 3:
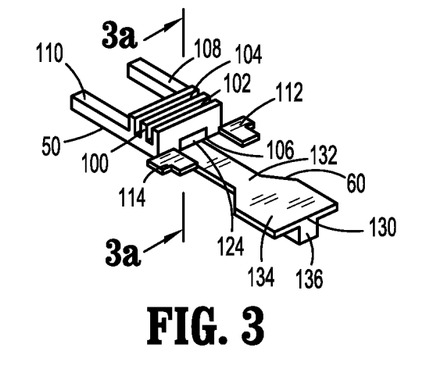
FIG. 3 is a perspective view of a cinch track and release bar of the buttressed anvil assembly.
Figure 3A:
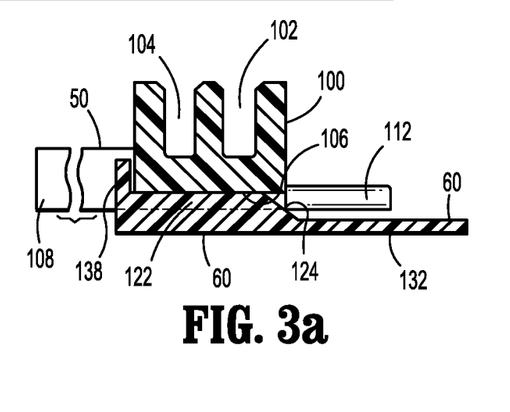
FIG. 3a is a side view, partially shown in section, taken along the line 3a-3a of FIG. 3.

The cinch track generally includes a body portion defining one or more tracks. Referring now to FIGS. 3 and 3a, cinch track 50 has a body portion 100 with first and second tracks 102 and 104. First and second tracks 102 and 104 are dimensioned to pinch or cinch first and second sides 54 and 56, respectively, of suture 32 to secure suture 32 to cinch track 50. Body portion 100 additionally includes a center slot 106 for receipt of release member 60 in a matter discussed in more detail hereinbelow.

As noted herein above, cinch track 50 is positioned within distal end 52 of anvil member 26 and is movable between first and second vertical positions relative to anvil member 26. As specifically shown in FIG. 3, a pair of distal arms 108 and 110 extend distally from body portion 100 while proximal tabs 112 and 114 extend proximally from body portion 100. Distal arms 108 and 110 are positioned against a proximal face 116 formed in distal end 52 of anvil member 26 (FIG. 2). Likewise, proximal tab 112 and proximal tab 114 are configured to loosely engage distal ends 118 and 120 of side walls 94 and 96 formed in anvil member 26 allowing cinch track 50 to move vertically within distal end 52 of anvil member 26 (FIG. 2).

Referring back for the moment to FIG. 2, as noted herein above, release member 60 is provided to move cinch track 50 between the first and second vertical positions. Release member 60 includes a distal wedge 122 which is configured to ride within center slot 106 of cinch track 50 to move cinch track 50 between the first and second vertical positions. A sloped face 124 extends proximally from distal wedge 122. Sides 126 and 128 of distal wedge 122 facilitate guiding distal wedge 122 against cinch track 50. In the embodiment of FIG. 3a, the bottom surface of the cinch track 50 is generally horizontal. However, in other embodiments, one or more surfaces can be shaped to cooperate with the sloped face 124, such as a cam surface, and may correspond to the shape of the sloped face 124.

Referring now to FIG. 3, release member 60 further includes a guide bar 130 extending proximally from distal wedge 122. Guide bar 130 includes a central portion 132 and a proximally extending flanged portion 134. Flanged portion 134 helps align release bar 60 within side walls 94 and 96 of anvil member 26. As shown, a guide rib 136 extends downwardly from guide bar 130 and is configured to ride within knife slot 28 such that release member 60 is movable in a longitudinal or horizontal direction relative to cinch track 50.

With specific reference to FIG. 3a, it can be seen that wedge 122 of release member 60 is configured to move body portion 100 of cinch track 50 vertically. Sloped face 124 of release member 60 facilitates assembly of anvil assembly 10, and specifically, allows for reset of release member 60 to pre-fire and assembly condition. A base stop 138 is provided on distal wedge 122 of release member 62 to prevent pulling wedge 122 completely through center slot 106 of cinch track 50 during assembly.

Referring now to FIGS. 2-7, and initially with regard to FIG. 2, the assembly of a strip of buttress material 30 to anvil member 26 will now be described. Proximal end 38 of strip of buttress material 30 is secured to proximal end 64 of anvil member 26. Specifically, proximal end 38 is positioned against an underside 140 of anvil member 26. Proximal suture 34 is manipulated such that first and second free ends 142 and 144 of first and second sides 72 and 74 pass through cutouts 44 and 46 to bring backspan 76 of proximal suture 34 into engagement with proximal end 38 of strip of buttress material 30.

Thereafter, first and second sides 72 and 74 are positioned within slots 68 and 70 in anvil member 26. During positioning, first and second side 72 and 74 are tensioned so as to secure proximal end 38 of strip of suture material 30 against underside 140 of anvil member 26. As noted herein above, slots 68 and 70 are dimensioned so as to pinch or cinch first and second sides 72 and 74. Once strip of suture material 30 has been secured, the excess material of first and second side 72 and 74 extending beyond slots 68 and 70 may be trimmed off through the cover. It should be noted that, since proximal end 38 of strip of suture material 30 stretches across knife slot 28, there is no need to release the tension on proximal suture 34 as it will be cut by a knife blade (not shown) during the stapling procedure.

With reference to FIGS. 2-7, the assembly of distal end 36 of strip of suture material 30 to anvil member 26 will now be described. Initially, with respect to FIGS. 3 and 3a, release member 60 is in a first or proximal most position. Cinch track 50 is in a first or vertically highest most position due to the passage and engagement of wedge 122 of release member 60 within slot 106 formed in body portion 100 of cinch track 50.

With reference to FIG. 2, distal end 36 of strip of buttress material 30 is positioned flush against underside 140 of anvil member 26. Distal suture 32 is manipulated such that free ends 146 and 148 of first and second sides 54 and 56, respectively, passed through cutouts 40 and 42 formed in distal end 36 of strip of buttress material 30. As shown, distal end 52 of anvil member 26 is provided with a pair of spaced apart holes 150 and 152. Free ends 146 and 148 of distal suture 32 are passed through holes 150 and 152 such that first and second sides 54 and 56 are aligned alongside first and second tracks 102 and 104 of cinch track 50. Vertical tension is applied to free ends 146 and 148 to secure distal end 36 of strip a buttress material 30 against underside 140 of anvil member 26.

Figure 6:
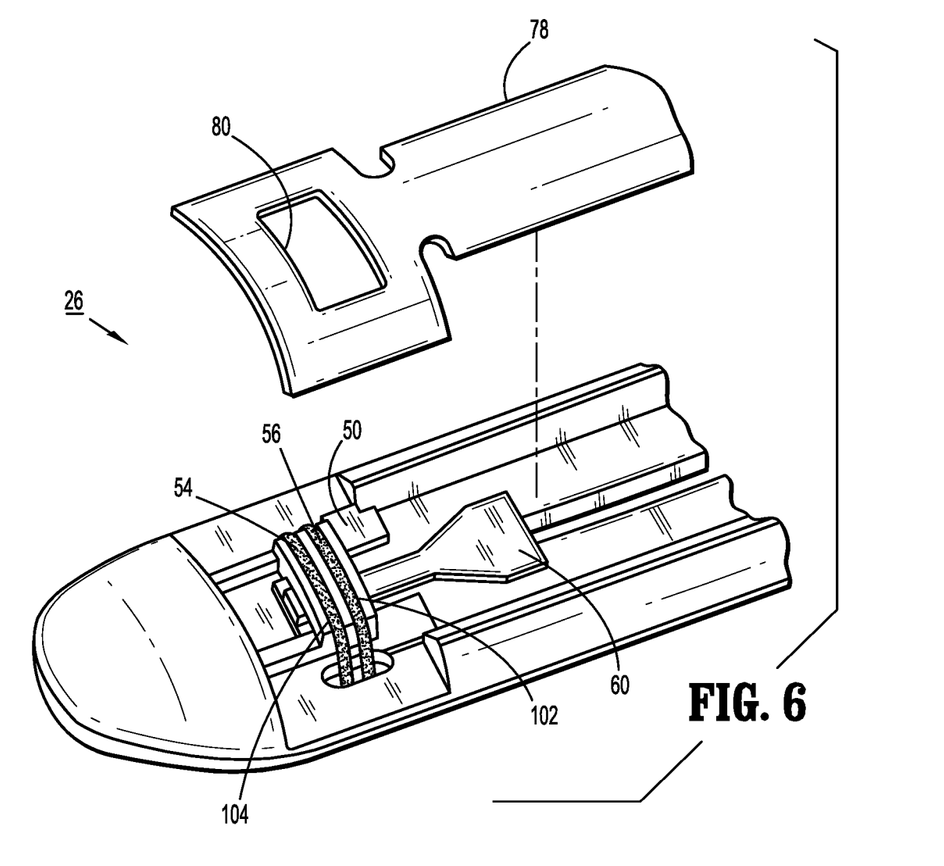
FIG. 6 is a perspective view similar to FIG. 4 with an anvil cover removed.
Figure 7:
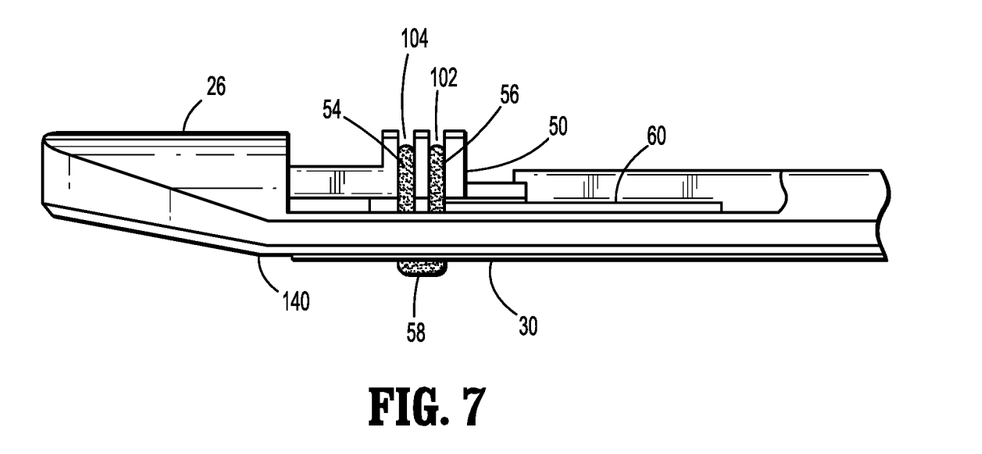
FIG. 7 is a side view of the distal end of the buttressed anvil assembly with the anvil cover removed.

First and second sides 54 and 56 are then manipulated such that first side 54 passes within second track 104 and second side 56 passes within first track 102 (see also FIGS. 6 and 7). As noted herein above, first and second tracks 102 and 104 are dimensioned so as to pinch or cinch a suture positioned therein. Thereafter, excess material of first and second sides 54 and 56 of distal suture 32 may be trimmed off. Finally, cover 78 is affixed to anvil member 26 in the manner described herein above.

Figure 4:
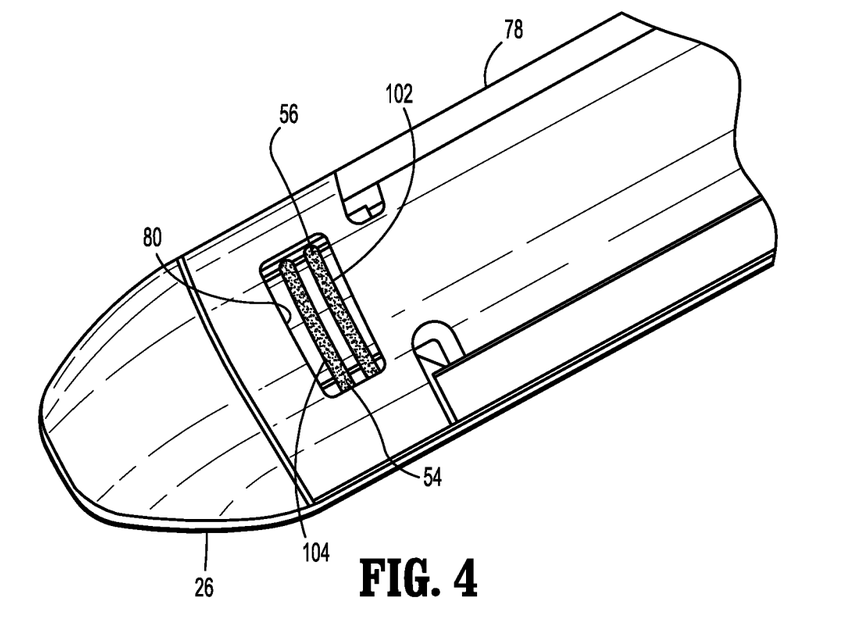
FIG. 4 is a perspective view of the distal end of the buttressed anvil assembly taken from the top.
Figure 5:
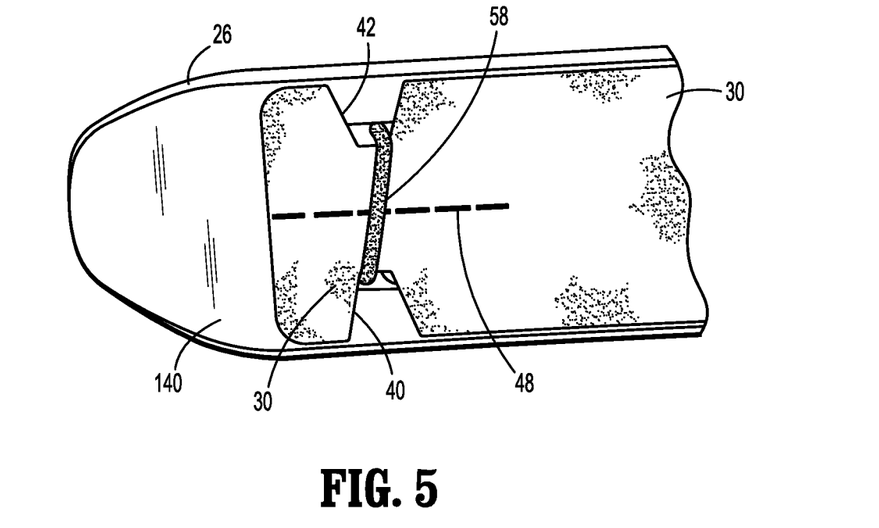
FIG. 5 is a perspective view of the distal end of the buttressed anvil assembly taken from the bottom.

With reference to FIGS. 4 and 5, in the assembled condition, first and second sides 54 and 56 of distal suture 32 are visible through distal cinch window 80 in cover 78 for verification (FIG. 4). Likewise, backspan 58 of distal suture 32 can be confirmed as extending across perforation line 48 and strip of suture material 30 (FIG. 5).

Referring now to FIGS. 1 and 6-10, the use of anvil assembly 10 will now be described. With reference to FIGS. 6 and 7, and as described herein above, in the initial position release bar 60 is in a first or proximal most position maintaining cinch track 50 in a first or vertically highest position relative to anvil member 26 thereby maintaining tension of backspan 58 of distal suture 32 against distal end 36 of strip of buttress material 30.

In use, with reference to FIG. 1, surgical stapling instrument 12 is manipulated such that anvil assembly 10 and staple cartridge 18 are positioned about the tissue (not shown) to be stapled. Once surgical stapling 12 has been properly positioned, trigger 22 is actuated to move anvil assembly 10 to the closed position about tissue relative to staple cartridge 18. While not specifically shown, anvil pockets are provided on anvil member 26 to clinch staples ejected out of staple cartridge 18 through the subject tissue and through strip of buttress material 30.

Figure 8:
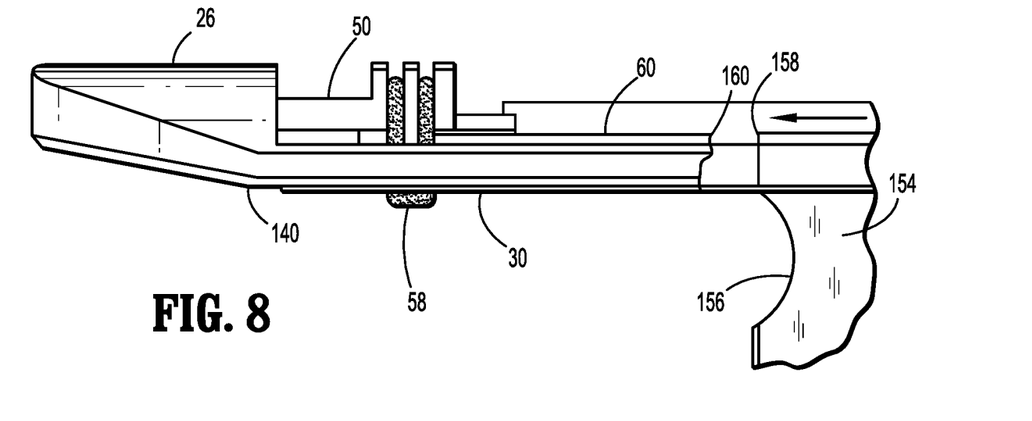
FIG. 8 is a side view similar to FIG. 7 during the initial advancement of a knife bar toward the release bar.

Referring back for the moment to FIG. 2, and as noted herein above, backspan 76 of proximal suture 34 extends across knife slot 28. Referring now to FIG. 8, a knife bar 154 is associated with surgical stapling instrument 12 to cut through staple lines formed in the tissue by staple cartridge 18 and anvil assembly 10. As knife bar 154 passes distally through knife slot 28 a blade 156 of knife bar 154 cuts through proximal end 38 of strip of buttress material 30 and severs backspan 76 a proximal suture 34. Continued advancement of knife bar 154 distally through slot 28, causes blade 156 to continue to cut through strip of buttress material 30.

Figure 9:
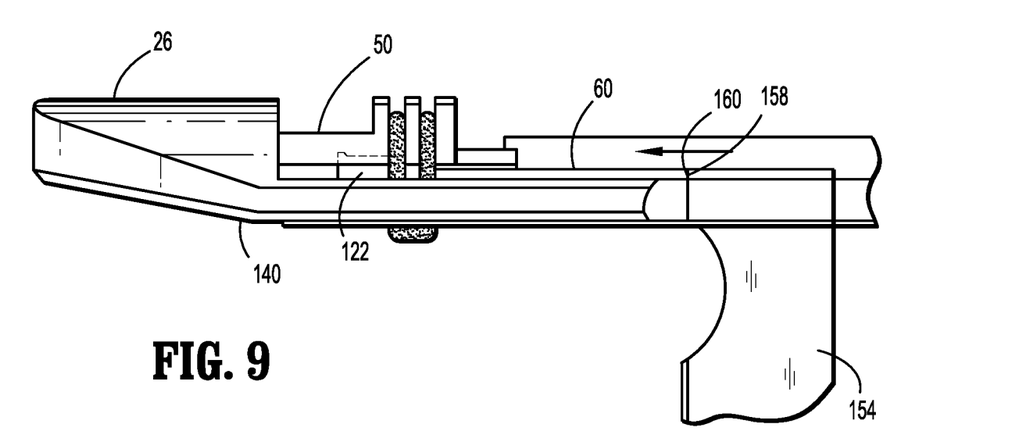
FIG. 9 is a side view similar to FIG. 8 illustrating the engagement of the knife bar with the release bar.

With continued reference to FIG. 8, as knife bar 154 advances distally through anvil member 26, a distal top edge 158 of knife bar 154 approaches a proximal edge 160 of release member 60. As best shown in FIG. 9, as distal edge 158 of knife bar 154 moves distally it engages proximal edge 160 of release member 60, knife bar 154 begins to drive release member 60 distally such that distal wedge 122 of release member 60 is driven distally through slot 106 (FIGS. 2 and 3) formed in cinch track 50.

Figure 10:
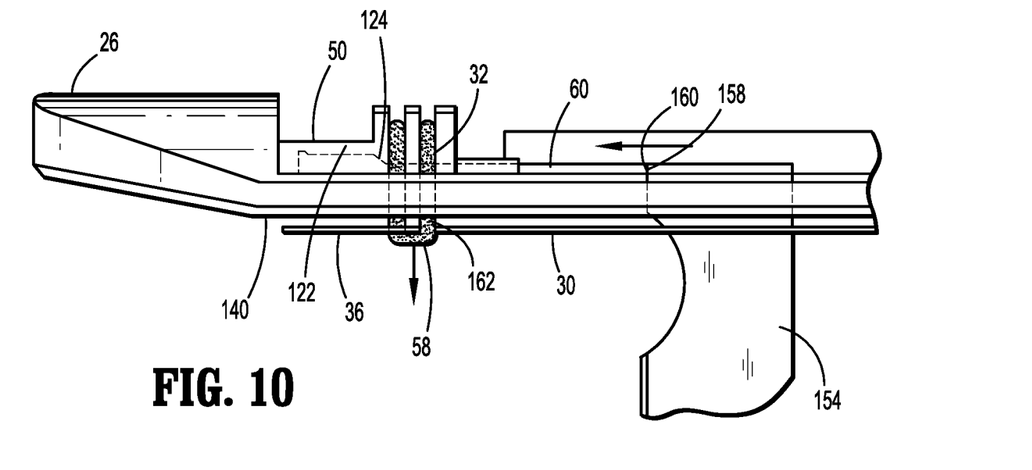
FIG. 10 is a side view similar to FIG. 8 illustrating the knife bar advancing the release bar through the cinch track to release tension on the strip of buttress material.

With specific reference to FIG. 10, as release member 60 is driven to a second or distal most position by a knife bar 54, sloped face 124 of distal wedge 122 clears slot 106 allowing cinch track 50 to drop down to a second or vertically lowest most position relative to anvil member 26. As shown, when cinch track 50 is in the second or vertically lowest position, tension is released on distal suture 32 such that backspan 58 of distal suture 32 drops a substantial distance below underside 140 of anvil member 26. This creates an opening or gap 162 between backspan 58 of distal suture 32 and underside 140 of anvil member 26.

Once knife bar 154 has reached a distal most position, pressure on trigger 22 may be released allowing anvil member 10 to move to the open position relative to staple cartridge 18 (FIG. 1). As anvil assembly 10 is moved to the open position, distal end 36 of strip of buttress material 30, being stapled the tissue, pulls free through gap 162 allowing distal end 36 to separate from anvil member 26. As noted herein above, and as shown in FIG. 2, perforation line 48 is formed in distal end 36 of strip of buttress material 30 allowing strip of buttress material 30 to separate into halves generally along the cut line formed by knife blade 156 through strip of buttress material 30. In this manner, anvil assembly 10 allows for simple and easy assembly of a strip of buttress material 30 to with anvil member 26 and, more importantly, allows for easy release of distal end 36 of a strip of buttress material 30 from anvil member 26.

It will be understood that various modifications may be made to the embodiments disclosed herein. For example, the release member could be arranged to be pulled proximally to change the position of the cinch track and release the suture and buttress. In other embodiments, the proximally pulled release member, or the release member 60 discussed above, may be connected to a separate actuator on the handle of the surgical instrument, for engagement by the user of the instrument. In another example, the disclosed cinch track may have more or fewer tracks to accommodate more or fewer wraps of a length of suture material. Further, the disclosed tensioning mechanisms, including the suture track and the release bar, may be adapted to be incorporated in a staple cartridge and to function with driving bars in the staple cartridge. Additionally, the disclosed methods and structure for releasing tension on a suture maintaining a strip of buttress material may find use in other forms of surgical staplers such as, for example, circular staplers, etc. In further embodiments, a release member pushes cinch track down vertically to release the tension on the suture and release the buttress. Therefore, the above description should not be construed as limiting, but merely as exemplifications of particular embodiments. Those skilled in the art will envision other modifications within the scope and spirit of the claims appended hereto.

What is claimed is:

1. A method for selectively securing a buttress material to an anvil assembly, the method comprising:
 moving a release member relative to an anvil member of the anvil assembly;

moving a track supported on the anvil member in response to movement of the release member; and changing a tension in a length of suture that secures the buttress material to the anvil member as the track moves relative to the anvil member.

2. The method of claim 1, wherein moving the release member relative to the anvil member includes advancing a knife blade into engagement with the release member.

3. The method of claim 2, wherein advancing the knife blade includes advancing the knife blade through a knife slot defined in the anvil member.

4. The method of claim 1, wherein moving the track supported on the anvil member includes moving the track in a direction transverse to the anvil member.

5. The method of claim 4, wherein moving the release member includes moving the release member in a longitudinal direction along the anvil member.

6. A surgical stapling apparatus, comprising:
a staple cartridge and an anvil assembly positioned for relative movement between one another;
a suture member;
a buttress material secured to the anvil assembly by the suture member; and
a track supported on the anvil assembly, the track selectively movable relative to anvil assembly to change a tension in the suture member.

7. The surgical stapling apparatus of claim 6, wherein the track is movable relative to the anvil assembly between a first position tensioning the suture member and a second position releasing the tension in the suture member.

8. The surgical stapling apparatus of claim 7, further comprising a release member movable relative to the anvil assembly to move the track.

9. The surgical stapling apparatus of claim 8, wherein the release member includes a wedge positioned to engage the track.

10. The surgical stapling apparatus of claim 6, wherein the suture member includes a first suture side and a second suture side that are connected to one another by a backspan.

11. The surgical stapling apparatus of claim 10, wherein the track includes a first track and a second track, the first track positioned to receive the first suture side, the second track positioned to receive the second suture side.

12. The surgical stapling apparatus of claim 10, wherein the anvil assembly defines first and second holes, the first suture side extending through the first hole, the second suture side extending through the second hole.

13. The surgical stapling apparatus of claim 6, wherein the buttress material includes a perforation to facilitate separation of at least a portion of the buttress material from the anvil assembly.

14. An anvil assembly, comprising:
an anvil member;
a suture member;
a buttress material secured to the anvil member by the suture member; and
a track supported on the anvil member, the track selectively movable relative to the anvil member to change a tension in the suture member.

15. The anvil assembly of claim 14, wherein the track is movable relative to the anvil member between a first position tensioning the suture member and a second position releasing the tension in the suture member.

16. The anvil assembly of claim 14, further comprising a release member movable relative to the anvil member to move the track.

17. The anvil assembly of claim 16, wherein the release member includes a wedge positioned to engage the track.

18. The anvil assembly of claim 14, wherein the suture member includes a first suture side and a second suture side that are connected to one another by a backspan, the backspan extending across the buttress material to support the buttress material adjacent to the anvil member.

19. The anvil assembly of claim 18, wherein the track includes a first track and a second track, the first track positioned to receive the first suture side, the second track positioned to receive the second suture side.

20. The anvil assembly of claim 19, wherein the anvil member defines first and second holes, the first suture side extending through the first hole, the second suture side extending through the second hole.

* * * * *